United States Patent
Wilson, Jr. et al.

[11] Patent Number: 5,540,668
[45] Date of Patent: Jul. 30, 1996

[54] ANTI-CROSS CONTAMINATION VALVE AND FLUID DELIVERY SYSTEMS USING SAME

[76] Inventors: Roland B. Wilson, Jr.; Glenda A. Wilson, both of 286 N. Wabash St. P.O. Box 725, Wabash, Ind. 46992

[21] Appl. No.: 375,849

[22] Filed: Jan. 20, 1995

[51] Int. Cl.$^6$ ..................................................... A61M 5/00
[52] U.S. Cl. ..................... 604/248; 604/80; 137/625.41; 137/625.47
[58] Field of Search ................................. 604/80, 9, 30, 604/32, 81, 245, 246, 247, 248, 256, 258, 323; 137/625, 625.12, 625.18, 625.42, 625.46, 625.41, 625.47

[56]  References Cited

U.S. PATENT DOCUMENTS

| | | | |
|---|---|---|---|
| 1,633,074 | 6/1927 | Mott | 604/32 |
| 3,048,192 | 8/1962 | Murphy, Jr. . | |
| 3,957,082 | 5/1976 | Fuson et al. | 604/80 X |
| 4,432,754 | 2/1984 | Urguhart et al. | 604/80 X |
| 4,703,775 | 11/1987 | Pastrone . | |
| 4,900,322 | 2/1990 | Adams . | |
| 4,950,230 | 8/1990 | Kendell | 604/248 X |
| 5,013,303 | 5/1991 | Tamari et al. . | |
| 5,059,173 | 10/1991 | Sacco | 604/80 |
| 5,336,174 | 8/1994 | Daoud et al. . | |
| 5,466,228 | 11/1995 | Evans | 604/248 |

*Primary Examiner*—Corrine M. McDermott
*Assistant Examiner*—N. Kent Gring
*Attorney, Agent, or Firm*—Liell & McNeil

[57]  ABSTRACT

An anti-cross contamination valve for use in medical fluid delivery systems comprises a valve housing having a first port, a second port, and a third port that open into a hollow interior. A valve body is rotatably mounted within the hollow interior and has at least one fluid passageway therethrough. A knob is attached to the valve body and extends outside of the valve housing. The at least one passageway includes a first fluid passageway that opens the first port to the third port when the valve body is rotated to a first position with respect to the valve housing. The second port is closed when the valve is in its first position. The at least one passageway also includes a second fluid passageway that opens the second port to the third port when the valve body is rotated to a second position with respect to the valve housing. The first port is closed when the valve is in its second position. In order to prevent the possibility of cross contamination, the valve also includes stop barriers and/or a special passageway/port geometry that prevents the possibility of the first port coming into fluid communication with the second port, or vice versa.

19 Claims, 3 Drawing Sheets

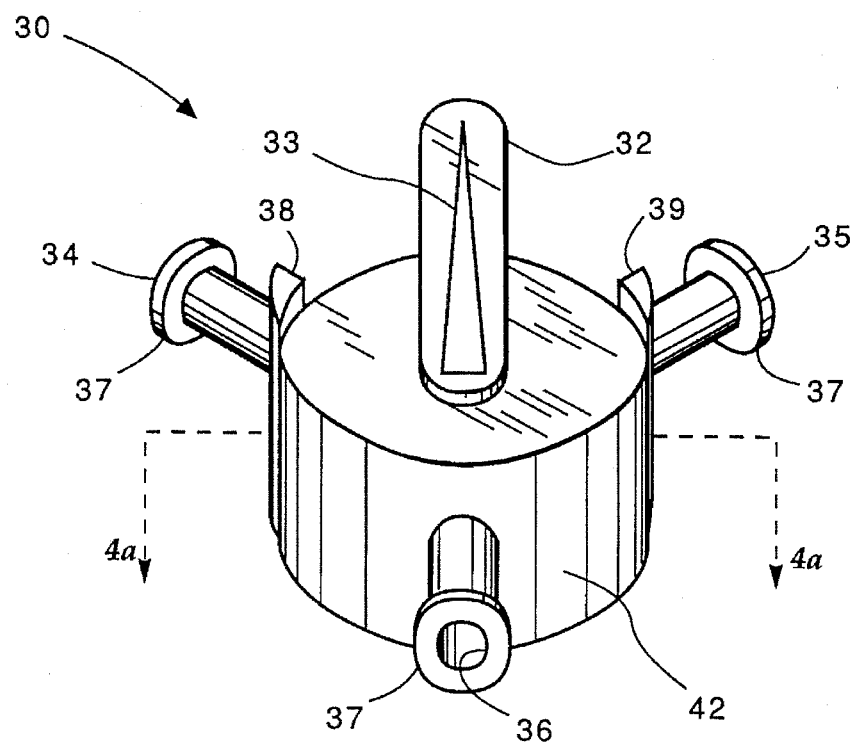
*Figure 3*
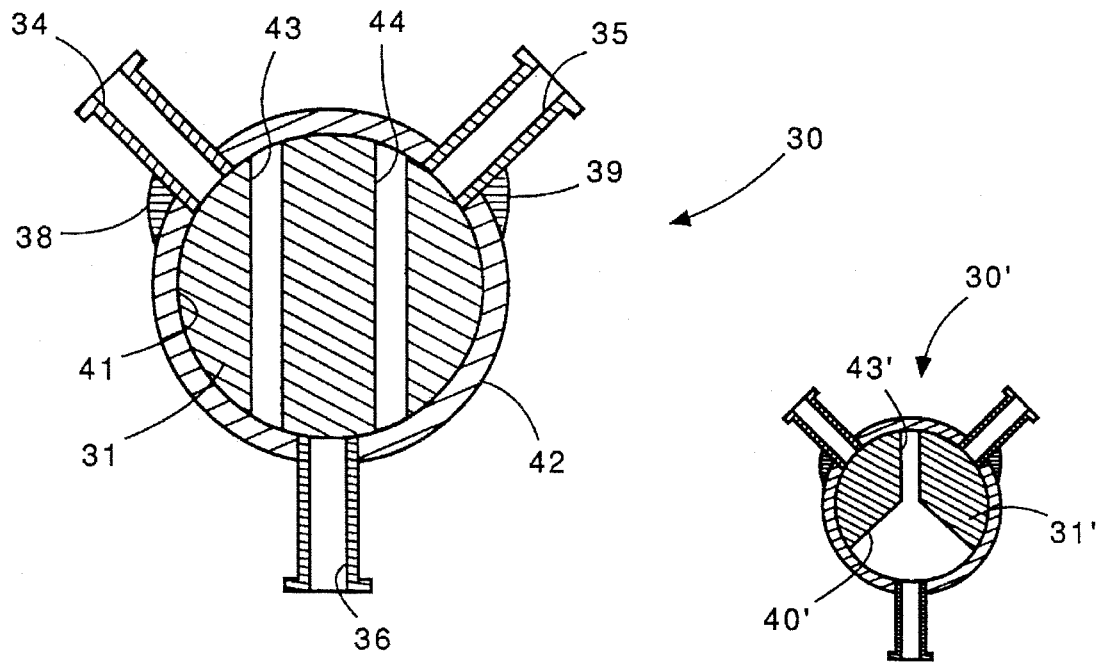
*Figure 4a*     *Figure 4b*

5,540,668

ANTI-CROSS CONTAMINATION VALVE AND FLUID DELIVERY SYSTEMS USING SAME

TECHNICAL FIELD

The present invention relates generally to medical fluid delivery systems, and more particularly to medical fluid delivery systems utilizing a valve that prevents cross contamination between fluid sources connected to the valve.

BACKGROUND OF THE INVENTION

Multi-port fluid transfer valves have long been known in the art. These valves typically have three or more ports and the ability to selectively open the various ports to one another in different combinations depending on the number of ports. For example, U.S. Pat. No. 3,048,192 to Murphy, Jr. shows a surgical valve with three or four ports and the ability to open any pair of ports to one another. Likewise, U.S. Pat. No. 4,900,322 to Adams shows a valve with four ports and the ability to selectively connect different pairs of the ports. While there are numerous medically related procedures in which it is desirable to cross connect various ports of a valve, there are some situations in which cross connection between certain ports creates the potential for undesirable cross contamination, undermining a particular medical procedure and/or preventing or delaying a patient from receiving a desired treatment.

FIG. 2 shows a prior art Y-type blood/solution set 10' utilized in a variety of circumstances to transfuse fluids to a patient. While these blood/solution sets work satisfactorily in many situations, physicians often encounter cross contamination problems when a solution bag connected to bag connector 16a is allowed to flow into the fluid container attached to connector 16b, or vice versa.

One example situation might be when blood/solution set 10' is being utilized to deliver a medicated saline solution from a first bag connected to connector 16a, and a sudden emergency requires the quick delivery of blood or blood product from a bag attached to connector 16b. In order to hasten the delivery of the blood to the patient, the physician may squeeze or mechanically compress the bag attached to connector 16b in order to increase the flow rate of fluid through the filter and other components downstream from the bag. Unfortunately, in many such emergency situations, both clamps 18a and 18b are accidentally left open and the blood flowing through connector 16b is permitted to flow down through Y-connector 20 and back up into the medicated saline solution bag attached to connector 16a, contaminating the medicated saline solution with whole blood or blood product. In this situation, the contaminated saline solution must be discarded, and the physician is left with guessing how much of the blood unit was lost to cross contamination. At the same time, the transfusion of emergency blood to the patient has been delayed because of the blood flowing across to the saline bag rather than down through the filter and other components to the patient. Further precious time will likely be wasted in the time it takes to close clamp 18a, remove the contaminated saline bag and attach a new medicated saline solution bag to connector 16a, which normally must be resumed after the blood unit has been delivered to the patient. While the prior art Y-type blood/solution set 10' and the valves discussed above have the ability to avoid cross contamination, they include no fail-safe means for preventing cross contamination.

The present invention is intended to overcome the potential cross contamination problems associated with the prior art fluid transfer medical devices.

SUMMARY OF THE INVENTION

In one embodiment, the present invention comprises an anti-cross contamination valve having a valve housing with a first port, a second port, and a third port that all open into a hollow interior. A valve body is rotatably mounted within the hollow interior and has at least one fluid passageway therethrough. A knob is attached to the valve body and extends outside of the valve housing. The at least one passageway includes a first fluid passageway that opens the first port to the third port when the valve body is rotated to a first position with respect to the valve housing, and closes the second port when the valve body is in its first position. Also, the at least one passageway includes a second fluid passageway that opens the second port to the third port when the valve body is rotated to a second position with respect to the valve housing, and the first port is closed when the valve body is in its second position. Finally, the valve includes some means for preventing the at least one fluid passageway from opening the first port to the second port.

BRIEF DESCRIPTION OF THE DRAWINGS

FIG. 3 is an isometric view of an anti-cross contamination valve according to the present invention.

FIG. 4a is a sectioned top view of the anti-cross contamination valve of FIG. 3 view along section line 4a—4a.

FIG. 4b is a sectioned top view of an anti-cross contamination valve according to another embodiment of the present invention.

DETAILED DESCRIPTION OF THE PREFERRED EMBODIMENT

Figure 2:
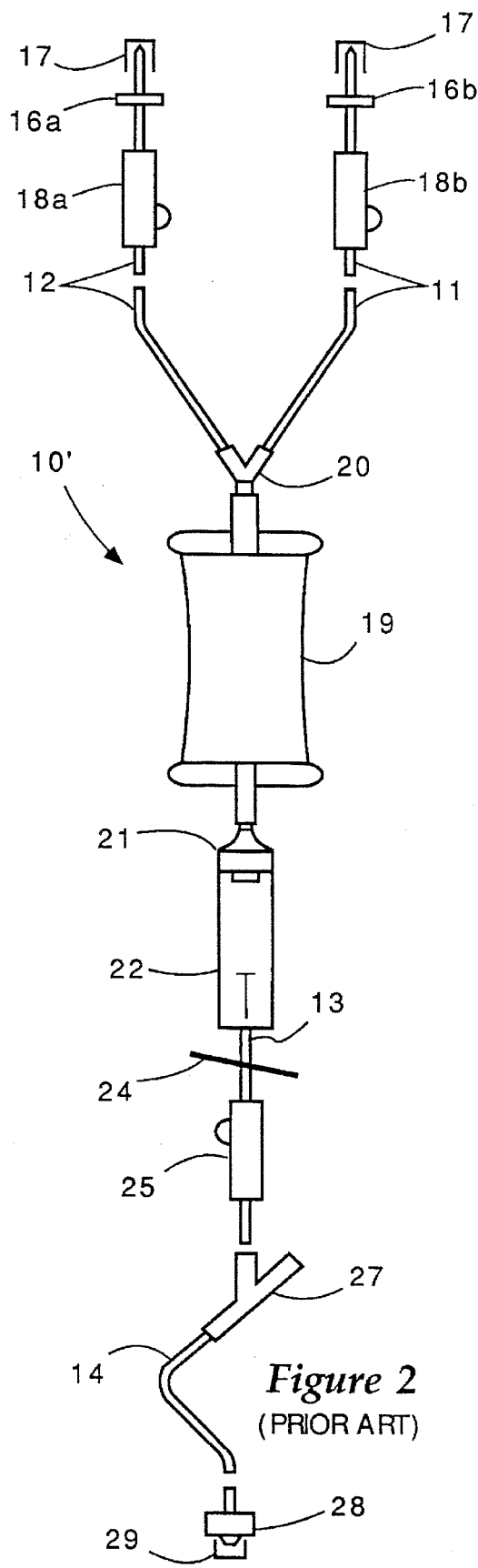
FIG. 2 is a schematic view of a Y-type blood/solution set according to the prior art.

Referring again to FIG. 2, a prior art Y-type blood/solution set 10' includes two lengths of IV tubing 11 and 12, each with a clamp 18 mounted thereon and having a bag connector 16 with a protective cap 17 attached to one of its ends. The other ends of tubing 11 and 12 merge into a Y-connector 20 that opens into a filter 19. A drop former 21 and drip chamber 22 are attached to the outlet end of the filter. A third length of IV tubing 13 extends from the bottom of drip chamber 22 to injection port 27. A slide clamp 24 and regulating or roll-type clamp 25 are mounted on IV tubing 13. Finally, a fourth length of IV tubing 14 is connected at one end to injection port 27 and at its other end to a connector 28, such as a Luer connector, that includes a protective cap 29, which is removed prior to use. In some Y-type blood/solution sets, the filter is omitted from the set. In such cases, an auxiliary filter can be attached intermediate the bag and bag connector 16 if needed.

Figure 1:
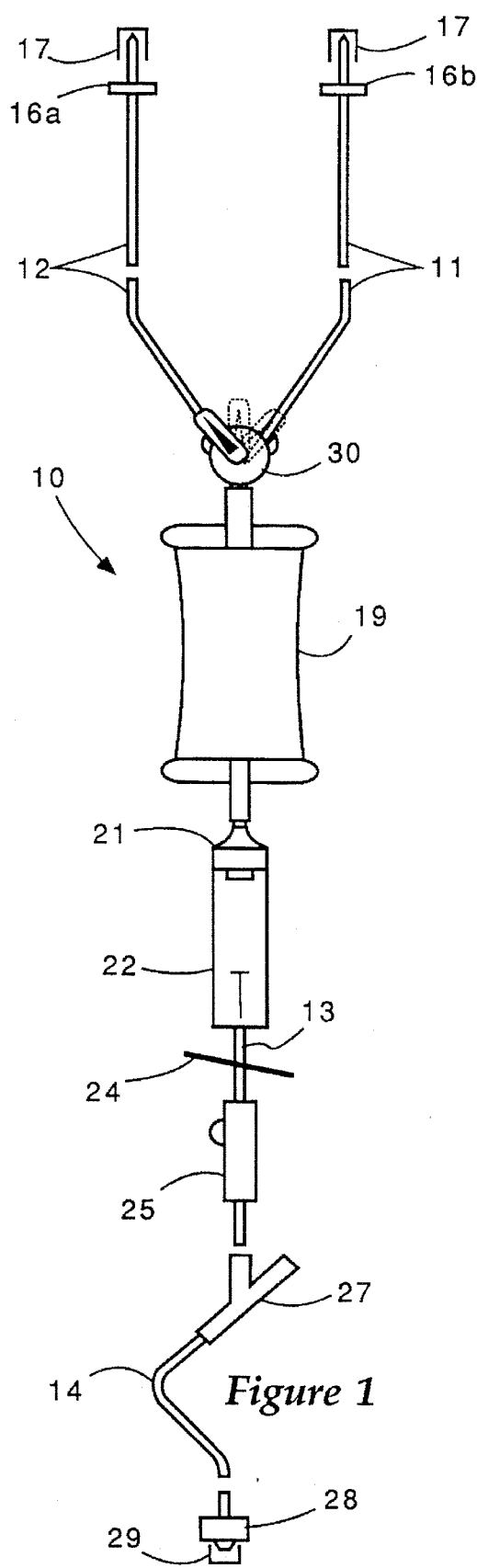
FIG. 1 is a schematic illustration of an anti-cross contamination Y-type blood/solution set according to one embodiment of the present invention.

Referring now to FIG. 1, an anti-cross contamination Y-type blood/solution set 10 according to the present invention is shown directly adjacent a prior art set 10'. Anti-cross contamination set 10 includes many of the same features, which are identically numbered, as its counterpart prior art set 10'. In particular, both sets include a first length of IV tubing 11 with a bag connector 16b attached to one end and connected to a first port of an anti-cross contamination valve 30 at its other end. Bag connector 16b can be any type of connector which facilitates connection of tubing 11 to a fluid container. For instance, connectors 16b might be an ordinary bag spike that includes a fluid tight protective cap 17, which is removed and discarded when bag connector 16b is actually attached to a fluid container, such as a blood or solution bag. A second length of tubing 12 likewise includes a bag connector 16a at one end and is attached to a second port of anti-cross contamination valve 30 at its other end. The outlet port of valve 30 is attached to a filter 19, which in turn is attached to a drop former 21 and a drip chamber 22. A third length of IV tubing 13 extends from the bottom of drip chamber 22 to an injection port 27. A typical slide clamp 24 and regulating clamp 25 are mounted on the third length of tubing 13. Regulating champ 25 has the ability to control the flow rate of fluid through the device to the patient, while slide clamp 24 gives the ability to quickly pinch off tubing 13 in order to shut off flow completely. Injection port 27 can be any type known that permits the injection of fluid or intravenous medication into the fluid flow through the set to the patient. A fourth length of IV tubing 14 is attached at one end to injection port 27 and to a connector 28, such as a Luer connector, at its other end. Until use, connector 28 preferably includes a protective end cap 29. As can be seen, anti-cross contamination set 10 is substantially identical to the prior art set 10' except that clamps 18a and 18b of the prior art set have been eliminated and the Y-connector 20 of the prior art has been replaced by an anti-cross contamination valve 30 according to the present invention.

Cross contamination between the respective fluid containers attached to connectors 16a and 16b is permitted in prior art sets 10' whenever both clamps 18a and 18b are left open, because Y-connector 20 is simply a three-way intersecting passageway. Anti-cross contamination set 10, on the other hand, includes a valve 30 which cannot permit fluid flow between the respective fluid containers attached to bag connectors 16a and 16b. Valve 30 is shown in its second position in which knob 32 and arrowhead 33 point in the direction of IV tubing 12. This indicates to the user that only the fluid container attached to bag connector 16a is in fluid communication with the filter 19 and other downstream components of the set. By rotating knob 32 to the right to its first position (shown in shadow) in which arrowhead 33 points in the direction of tubing 11, the user knows that only tubing 11 is then open to flow through the valve. Also shown in shadow in FIG. 1 is knob 32 of valve 30 in its middle or third position in which both the inlet port connected to tubing 12 and the inlet port connected to tubing 11 are closed to filter 19 and the other lower components of the set. Thus the user of anti-cross contamination Y-type set 10 can quickly tell which, if any, of the fluid containers attached to bag connector 16a and 16b are open to flow, by merely glancing at the position of arrowhead 33 on valve 30. This is not possible with the prior art set 10' which left the user guessing which, if any, of the fluid containers are open to flow based upon a glance at the relative position of the rollers in clamps 18a and 18b.

Clamps 18a and 18b of the prior art permit one to regulate the rate of flow to filter 19. Flow regulation in anti-cross contamination Y-type set 10 is accomplished simply by rotating knob 32 slightly toward the middle closed position so that the internal passage through valve 30 is only partially opened to the respective port. (See FIG. 4).

The various features and internal structure of anti-cross contamination valve 30 are illustrated in FIGS. 3 and 4a. Valve 30 includes a cylindrically shaped valve housing 31 having a first inlet port 34, a second inlet port 35 and an outlet port 36 that all open into a hollow interior 41. Each of the ports includes a connector 37, such as a Luer lock connector, which facilitate attachment of the various ports to a length of tubing. A cylindrically shaped valve body 31 is sized and positioned to substantially fill hollow interior 41. Valve body 31 includes a first passageway 43 and a second passageway 44 therethrough that are substantially parallel to one another. A knob 32 is attached to the upper side (not shown) of valve body 31, and facilitates rotation of the same within hollow interior 41. The various components of valve 30 are preferably molded from a suitable plastic of a type known in the art.

FIGS. 3, 4a and 4b show the valve in its closed position so that neither first inlet port 34 nor second inlet port 35 are open to outlet port 36. Stop barriers 38 and 39 restrict the rotational movement of valve body 31 within valve housing 42. In particular, since knob 32 extends over the side of valve housing 42, counterclockwise rotation of valve body 31 is stopped when knob 32 encounters left stop barrier 38, as shown in FIG. 1. When in this position, the passageway 43 permits fluid communication between first inlet port 34 and outlet port 36. Likewise, clockwise rotation of valve body 31 is stopped when knob 32 encounters right stop barrier 39. Valve 30 can be operated with one hand by simply placing one finger on one of the stops 38 or 39 and another finger on the side of knob 32, and then simply pinching the fingers toward one another until knob 32 abuts one of the stops. Flow through valve 30 can be slowed or regulated by rotating knob 32 slightly away from one of the respective stop barriers so that only part of the passageway 43 or 44 is in fluid communication with the respective inlet port. Thus, the valve of the present invention permits selective fluid connection through the valve, regulation of that flow, and includes features that prevent the possibility of cross contamination between the inlet ports to the valve.

FIG. 4a shows a valve interior 31 corresponding to the preferred embodiment of the anti-cross contamination valve of the present invention, and FIG. 4b shows an alternative embodiment 30' having a single passageway therethrough. Valve 30' includes only a single passageway 40' instead of the parallel passages 43, 44 of the earlier embodiment. Valve 30' is similar in operation to the earlier embodiment in that one simply rotates valve body 31' via the attached knob (see FIG. 3) in order to point upper portion 43' of passageway 40' toward one of the respective ports. Also like the earlier embodiment, side stops prevent valve body 31' from being positioned to permit cross contamination between the inlet ports. Alternative valve anti-cross contamination valve 30' is less desirable than valve 30 of FIGS. 3 and 4a because passageway 40' can in some cases allow the undesirable collection of fluid within the valve.

Figure 5:
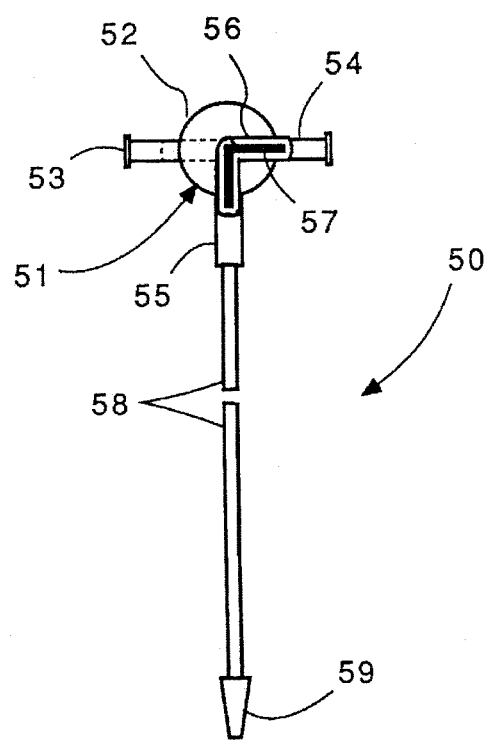
FIG. 5 is a top view of an anti-cross contamination extension tubing/valve assembly according to another embodiment of the present invention.

Referring now to FIG. 5, an anti-cross contamination extension tubing/valve assembly 50 according to the present invention is illustrated. Assembly 50 includes an anti-cross contamination valve 51 with a first port 53, a second port 54 and a third port 55 which is connected to a length of IV tubing 58. If desirable, a connector 59, of a type known in the art, can be attached to the other end of IV tubing 58. Valve 51 is similar in function to the anti-cross contamination valve 30 discussed earlier except that it includes a single elbow passageway (not shown) which aligns with indicia 57 on knob 56. Because first port 53 and second port 54 in valve body 52 are aligned, it is impossible for these two ports to be in fluid communication with one another through the elbow passageway, since both inlet ports 53 and 54 are substantially orthogonal to outlet port 55. Thus, the fluid sources connected to first port 53 and second port 54 cannot cross contaminate one another since there is no way to open a fluid passageway between these respective ports regardless of the position of knob 56. FIG. 5 also shows knob 56 in shadow rotated clockwise 90° to the position in which first port 53 is opened to third port 55. Flow regulation through valve 51 is accomplished by simply rotating knob 56 slightly off its fully opened position as shown so that only a portion of the passageway within valve body 52 is exposed to the respective ports. Unlike valves 30 and 30' discussed earlier, valve 51 includes no barriers so that knob 56 can rotate 360°; however, the user can quickly note the position of the valve by observing the relative positioning of indicia 57 relative to the respective ports 53, 54 and 55.

Figure 6:
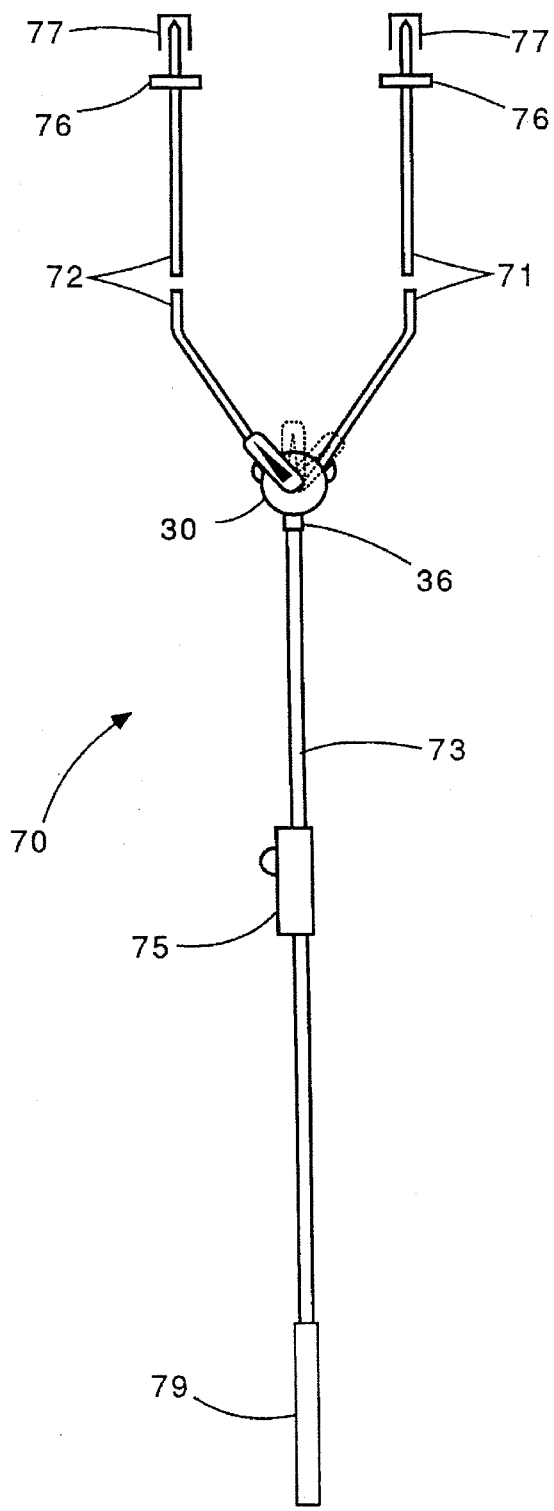
FIG. 6 is a schematic illustration of an anti-cross contamination urological irrigation set according to still another embodiment of the present invention.

Referring now to FIG. 6, an anti-cross contamination urological irrigation set 70 according to the present invention is shown. Urological set 70 is substantially similar to the anti-cross contamination Y-type blood/solution set 10 discussed earlier, except that it preferably includes larger diameter irrigation tubing instead of the IV tubing of set 10, and also eliminates various components that are included in the blood/solution set 10 of the earlier embodiment. In particular, urological set 70 does not include a filter, drop former, injection port or drip chamber.

Urological set 70 includes a first length of irrigation tubing 71 having an appropriate connector 76 attached to one end and a port of anti-cross contamination valve 30 attached to its other end. Likewise, a second length of irrigation tubing 72 has an appropriate connector 76 attached to one end and another port of anti-cross contamination valve 30 attached to its other end. Preferably, both connectors include a protective fluid tight cap 77 that remains in place until use, at which time they are removed and discarded. A third length of irrigation tubing 73 has one end connected to outlet port 36 of valve 30 and its other end connected to a connector 79 of a type known in the art, such as a catheter adapter. A regulating clamp 75 is mounted on the third length of irrigation tubing 73 and acts as a secondary means of controlling the flow rate through the set.

Although the present invention has been illustrated as an anti-cross contamination urological set, extension tubing/valve assembly, a Y-type blood/solution set and an anti-cross contamination valve, it should be clear that various other modifications can be made to the present invention as herein above described and many apparently different embodiments of the same can be made without departing from this scope of the invention. For instance, various known fluid delivery components (i.e., clamps, tubing, filters, connectors, etc.) can be assembled in various combinations with the anti-cross contamination valve of the present invention to produce a wide variety of medical fluid delivery systems needing a fail-safe against cross contamination. The following is a partial list of some such medical fluid delivery systems which could utilize the anti-cross contamination valve of the present invention: nutritional pump sets, vented Y-type blood pump sets, arthroscopic irrigation fluid pump sets, cardiac catheterization set, hypodermoclysis sets, Y-type connecting sets, venoset piggyback sets, irrigation Y-connectors, 4-lead transurethral resection sets, cystomanometer sets, Y-type blood volumetric pump sets, Y-type catheter extension sets, mass infusion sets, acute peritoneal dialysis administration/drainage sets, Y-type wound irrigation sets, laparoscopic suction-irrigation sets, primary Y-type blood transfusion sets and endoscopic irrigation sets. Thus, the present invention finds potential application in a wide variety of medical procedures including those relating to transurethral resection, endourology, arthoscopy, endoscopy, laparoscopy, endo-surgery, pelviscopic surgery, hysteroscopic surgery, to name but a few. Furthermore, those skilled in the art will immediately appreciate that the principals of the present invention can be applied to produce anti-cross contamination valves having four or more ports, instead of three ports as shown in the described embodiments. The above description is intended to serve only to aid those skilled in an art and an understanding of the invention and is not intended to limit the legal scope of the patent which is described solely by the claims as set forth below:

We claim:

1. An anti-cross contamination valve comprising:

a valve housing having only a plurality of first ports and a third port different from said plurality of first ports that all open into a hollow interior;

a valve body rotatably mounted within said hollow interior and having at least one fluid passageway therethrough;

a knob attached to said valve body and extending outside of said valve housing;

said at least one passageway including a first fluid passageway that opens a first port of said plurality of first ports to said third port when said valve body is rotated to a first position with respect to said valve housing, all of said plurality of first ports, except said first port, being closed when said valve body is in said first position;

said at least one passageway including a second fluid passageway that opens a second port of said plurality of first ports to said third port when said valve body is rotated to a second position with respect to said valve housing, all of said plurality of first ports, except said second port, being closed when said valve body is in said second position; and means for preventing said at least one fluid passageway from opening any of said plurality of first ports to one another.

2. The anti-cross contamination valve of claim 1, wherein said valve body has a third position that closes all of said plurality of first ports to said third port.

3. The anti-cross contamination valve of claim 2, wherein said at least one passageway includes an elbow passageway; and said first port is substantially aligned with said second port, which are both substantially orthogonal to said third port.

4. The anti-cross contamination valve of claim 2, wherein said knob includes an indicia that points at said first port when said valve body is in said first position and points at said second port when said valve body is in said second position.

5. The anti-cross contamination valve of claim 4, wherein said preventing means includes said valve housing having a first stop barrier and a second stop barrier;

said valve body being restricted to rotating between said first stop barrier and said second stop barrier.

6. The anti-cross contamination valve of claim 5, wherein said at least one passageway, said first passageway and said second passageway are a single passageway.

7. The anti-cross contamination valve of claim 4, wherein said first passageway is substantially parallel to said second passageway.

8. An anti-cross contamination Y-type blood/solution set comprising:

a first length of tubing having a bag connector mounted on one end;

a second length of tubing having a bag connector mounted on one end;

an anti-cross contamination valve having a plurality of first ports that include a first port and a second port, said first port being attached to the other end of said first length of tubing, said second port being attached to the other end of said second length of tubing, said valve also having a third port different from said plurality of first ports and means for preventing fluid flow between any of said plurality of first ports;

a drop former attached to said outlet port;

a drip chamber attached to said drop former;

a third length of tubing with one end attached to said drip chamber and an injection port mounted on its other end;

a clamp mounted around said third length of tubing; and a fourth length of tubing with one end attached to said injection port and a connector on its other end.

9. The anti-cross contamination Y-type blood/solution set of claim 8, wherein said valve includes:

a valve housing having said first port, said second port and said third port that open into a hollow interior;

a valve body rotatably mounted within said hollow interior and having at least one fluid passageway therethrough;

a knob attached to said valve body and extending outside of said valve housing;

said at least one passageway including a first fluid passageway that opens said first port to said third port when said valve body is rotated to a first position with respect to said valve housing, all of said plurality of first ports, except said first port, being closed when said valve body is in said first position;

said at least one passageway including a second fluid passageway that opens said second port to said third port when said valve body is rotated to a second position with respect to said valve housing, all of said plurality of first ports, except said second port, being closed when said valve body is in said second position; and means for preventing said at least one fluid passageway from opening any said plurality of first ports to one another.

10. The anti-cross contamination Y-type blood/solution set of claim 9, wherein said valve body has a third position that closes all of said plurality of first ports to said third port.

11. The anti-cross contamination Y-type blood/solution set of claim 10, wherein said knob includes an indicia that points at said first port when said valve body is in said first position and points at said second port when said valve body is in said second position.

12. The anti-cross contamination Y-type blood/solution set of claim 11, wherein said preventing means includes said valve housing having a first stop barrier and a second stop barrier;

said valve body being restricted to rotating between said first stop barrier and said second stop barrier.

13. The anti-cross contamination Y-type blood/solution set of claim 12, wherein said at least one passageway, said first passageway and said second passageway are a single passageway.

14. An anti-cross contamination valve consisting essentially of:

a valve housing having only three ports that includes a first port, a second port and a third port that open into a hollow interior;

a valve body rotatably mounted within said hollow interior and having at least one fluid passageway therethrough;

a knob attached to said valve body and extending outside of said valve housing;

said at least one fluid passageway including a first fluid passageway that opens said first port to said third port when said valve body is rotated to a first position with respect to said valve housing, said second port being closed when said valve body is in said first position;

said at least one fluid passageway including a second fluid passageway that opens said second port to said third port when said valve body is rotated to a second position with respect to said valve housing, said first port being closed when said valve body is in said second position; and means for preventing said at least one fluid passageway from opening said first port to said second port.

15. The anti-cross contamination valve of claim 14, wherein said valve body has a third position that closes said first port and said second port to said third port.

16. The anti-cross contamination valve of claim 15, wherein said preventing means includes said valve housing having a first stop barrier and a second stop barrier;

said valve body being restricted to rotating between said first stop barrier and said second stop barrier.

17. The anti-cross contamination valve of claim 15, wherein said at least one passageway, said first fluid passageway and said second fluid passageway are a single passageway.

18. The anti-cross contamination valve of claim 15, wherein said at least one fluid passageway includes an elbow passageway; and said first port is substantially aligned with said second port, which are both substantially orthogonal to said third port.

19. The anti-cross contamination valve of claim 15, wherein said first fluid passageway is substantially parallel to said second fluid passageway.

* * * * *